United States Patent [19]

Galantay et al.

[11] 4,011,339
[45] Mar. 8, 1977

[54] HYPOLIPIDEMIC ALLENE CARBOXYLIC ACIDS

[75] Inventors: Eugene E. Galantay, Liestal, Switzerland; Faizulla G. Kathawala, West Orange, N.J.

[73] Assignee: Sandoz, Inc., E. Hanover, N.J.

[22] Filed: Aug. 15, 1975

[21] Appl. No.: 605,040

[52] U.S. Cl. .................. 424/317; 260/332.2 A; 260/470; 260/473 R; 260/473 F; 260/476 R; 260/515 R; 260/516; 260/520 D; 260/521 R; 424/275; 424/308
[51] Int. Cl.² ..................................... A61K 31/19
[58] Field of Search ................. 424/317; 260/521 R

[56] References Cited
OTHER PUBLICATIONS

Chemical Abstracts, 68:68292f (1968).
Chemical Abstracts, 64:19474d (1966).

*Primary Examiner*—Leonard Schenkman
*Attorney, Agent, or Firm*—Gerald D. Sharkin; Richard E. Vila; Frederick H. Weinfeldt

[57] ABSTRACT

The compounds are 4-aryl substituted buta-2,3-dienoic acids and esters thereof which may also be lower alkyl-substituted at any of the 2- and 4-positions, e.g., 4-(p-methoxyphenyl)-2-methyl-buta-2,3-dienoic acid. The compounds are useful as pharmaceuticals, e.g., as anti-inflammatory agents and hypolipidemic agents.

32 Claims, No Drawings

HYPOLIPIDEMIC ALLENE CARBOXYLIC ACIDS

This invention relates to carboxylic compounds, and more particularly to 4-aryl-substituted-buta-2,3-dienoic acids and esters thereof and their preparation, as well as to pharmaceutical compositions containing such compounds and the use of such compounds.

The compounds involved in this invention may be conveniently represented by the formula I:

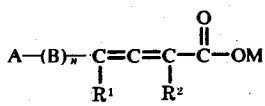

wherein $n$ is 0 or 1;
A is

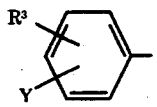

wherein Y is a hydrogen atom, alkyl having from 1 to 4 carbon atoms, alkoxy having from 1 to 24 carbon atoms, alkylthio having from 1 to 24 carbon atoms, preferably thiomethyl, halo having an atomic weight of from about 19 to 36, i.e., fluoro or chloro, cyclohexyl, phenoxy or substituted or unsubstituted phenyl of the formula

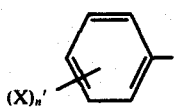

wherein X is a hydrogen atom, halo having an atomic weight of from about 19 to 36, i.e., fluoro or chloro, alkoxy having from 1 to 4 carbon atoms or alkyl having from 1 to 4 carbon atoms, preferably a hydrogen atom;
$n'$ is an integer from 1 to 2, preferably 1; or when $n$ is 0 A is

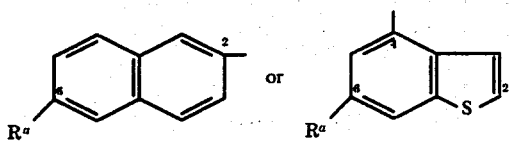

wherein $R^a$ is hydrogen, halogen having an atomic weight of from about 19 to 36, i.e., fluoro, or chloro, alkyl having from 1 to 4 carbon atoms, alkoxy having from 1 to 4 carbon atoms, preferably methoxy, alkylthio having from 1 to 4 carbon atoms, or difluoromethoxy;
B is

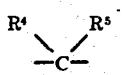

wherein each of $R^4$ and $R^5$ is, independently, alkyl having from 1 to 3 carbon atoms, preferably methyl, each of $R^1$ and $R^2$, independently, is a hydrogen atom or alkyl having from 1 to 4 carbon atoms;
$R^3$ is a hydrogen atom, alkyl having from 1 to 3 carbon atoms or halo having an atomic weight of from about 19 to 36, i.e., fluoro, or chloro; and
M is a hydrogen atom, (or a cation forming a pharmaceutically acceptable salt), or alkyl having from 1 to 3 carbon atoms, preferably ethyl.

With reference to the definitions of alkyl, alkoxy and akylthio above, it is understood that when any of them have from 1 to 3 carbon atoms, the alkyl portion thereof may be methyl, ethyl, n-propyl or isopropyl, and when any of them have from 1 to 4 carbon atoms, the alkyl portion thereof includes the above enumerated alkyl groups as well as n-butyl, isobutyl and tertiary butyl. Where Y is alkoxy or alkylthio of 1 to 24 carbon atoms, two classes are contemplated, i.e. the class having from 1 to 4 carbon atoms (a lower alkyl moiety) and those having from 5 to 24 carbon atoms (i.e. a higher alkyl moiety, such as pentyl, decyl, dodecyl, tetradecyl, hexadecyl and octadecyl), which may be branched or unbranched, preferably having from 5 to 16 carbon atoms.

The class of Compounds I consists of two sub-classes, depending upon the nature of M, i.e., Compounds Ia when M is alkyl and Compounds Ib when M is a hydrogen atom.

Certain of Compounds I wherein A is unsubstituted phenyl are described in the literature, e.g., J. Chem. Soc. 1956, 4764, Chem. Berichte, 99, 1198 (1966), and Liebigs Ann. Chem. 756, 112 (1972). However, no pharmaceutical utility is disclosed for the described compounds. Thus, an embodiment of this invention is the use of all Compounds I as anti-inflammatory agents and as hypolipedemic agents. Another embodiment of the invention is Compounds I', which are the same as Compounds I, provided that when $n$ is 0, then A is other than unsubstituted phenyl.

Some compounds I described in the literature are:
1) 4-phenyl-buta-2,3-dienoic acid (m.p. 88° to 91° C. from ether/pentane);
2) ethyl 2-methyl-4-phenyl-penta-2,3-dienoate (b.p. 75° – 80° C., at 0.025 mm Hg);
3) 2-methyl-4-phenyl-penta-2,3-dienoic acid (m.p. 111°–112° C. from ligroin);
4) 2-methyl-4-phenyl-buta-2,3-dienoic acid (m.p. 120° – 122° C. for ligroin); and
5) 4-phenyl-penta-2,3-dienoic acid.

Compounds I which are preferred are those wherein $n=0$, each of $R^3$ and M is a hydrogen atom, (or a salt-forming cation), and Y is at the para-position; particularly where A is para-substituted phenyl, more particularly where A is p-thioalkylphenyl, or p-alkoxyphenyl.

Compounds I may be prepared by adapting procedures described in the literature for preparing those Compounds I which are known. A convenient method for preparing Compounds Ia is a procedure comprising two steps.

The first step is a Wittig reaction (Process a[1]), i.e., a reaction of a ketene of the formula II:

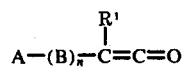

wherein A, B, n and $R^1$ are as defined above, with a Wittig reagent of formula IIIa or IIIb:

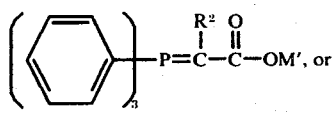

IIIa

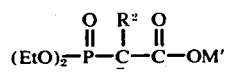

IIIb wherein $R^2$ is as defined above, and $M'$ is $M$ when it is alkyl, to form a phosphorous-containing intermediate, which is then subjected to rearrangement-decomposition (Process $a^2$). (Process $a^1$) is suitably carried out under anhydrous conditions in an inert organic solvent, e.g., a hydrocarbon such as benzene or toluene, or an ether such as diethyl ether, tetrahydrofuran, or dimethoxyethane (diglyme), at moderate temperatures, e.g., about $-5°$ to $200°$ C., preferably at about $20°$ to $30°$ C. or at the reflux temperature of the solvent. The phosphorous-containing intermediates obtained by Process $a^1$ are of varying stability. In some instances they are relatively stable and may be recovered from the reaction mixture and refined before being subjected to decomposition-rearrangement.

Process $a^2$ may be accomplished at elevated temperatures, i.e., about 50 to 200° C., by heating in an inert solvent, e.g., at the reflux temperature of the solvent. Suitable solvents are those suitable for the first step (Process $a^1$.) It is convenient to accomplish Process $a^2$, i.e., to convert the intermediates obtained by Process $a^1$, to their corresponding Compounds Ia merely by heating the reaction mixture obtained by Process $a^1$, (containing the resultant phosphorous-containing intermediate, without recovery thereof), e.g., at the reflux temperature of the mixture and then recovering the resultant Compound Ia. When process $a^1$ is carried out at higher temperatures, i.e. those of Process $a^2$, then an intermediate formed by Process $a^1$ may be rapidly converted to a product of Process $a^2$).

If a phosphorous-containing intermediate is recovered from the reaction mixture it may be converted to its corresponding Compound Ia by heating, i.e., at about 50° to 300° C., under vacuum (Process $a^{2'}$). A convenient method of carrying out Process $a^{2'}$ at higher temperatures, e.g. at over 180° C., is by short path distillation-pyrolysis (under vacuum, e.g., 0.05 to 0.3 mmHg). In some cases where $R^2$ is a hydrogen atom, heating yields a corresponding alkynyl ester isomer of the desired Compound Ia, i.e., a compound of the formula Ia':

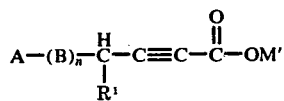

Ia' wherein A, B, $n$, $R^1$ and $M'$ are as defined above, rather than the desired Compound Ia. The isomerization (Process $a^3$) of a Compound Ia' to its corresponding Compound Ia may be carried out in a suitable solvent with a strong non-aqueous inorganic base, at moderate temperatures, e.g., from about 10° to 35° C., preferably at from 20° to 30° C. The inorganic base may be an alkoxide (having from 1 to 3 carbon atoms) of sodium or potassium, e.g. sodium methoxide or potassium methoxide, in which case the solvent is an absolute alkanol having from 1 to 3 carbon atoms, preferably having the same number of carbon atoms at the alkoxide. The amount of base present is not critical and can be as low as a catalytic amount. Process $a^3$ may be analogously carried out using by replacing the non-aqueous inorganic base with an aqueous inorganic base such as 2 to 10% solution of an alkali metal hydroxide, e.g., sodium hydroxide or potassium hydroxide, at temperatures of, for example, from about 15° to 120° C., in the presence of a water-miscible solvent such as a lower alkanol, e.g., having from 1 to 3 carbon atoms, such as methanol or ethanol. Where such reaction is carried out under aqueous basic conditions, saponification as well as isomerization occurs and the product is therefore in the acid form, i.e., a Compound Ib (Process $a^{2'}$). Compounds I obtained by Process $a^3$ are compounds $Ia^1$, i.e., Compounds Ia in which $R^2$ is a hydrogen atom. Compounds I obtained by Process $a^{2'}$ are Compounds $Ib^1$, i.e., Compounds Ib in which $R^2$ is a hydrogen atom.

It will be appreciated that the saponifying conditions of Process $a^{3'}$ may be applied to a Compound Ia to saponify it to its corresponding acid, i.e., a Compound Ib, where such is desired.

Compounds IIIa and IIIb are known, some being commercially available, or where not known are obtainable by procedures analogous to those described for the preparation of the known compounds. Compounds IIIb may be provided in the form of their sodium salts by treatment of a dialkyl alkoxy carbonyl alkyl phosphonate (Compounds IIIb') with a strong alkali metal base, such as the hydride or amide of sodium, potassium or lithium; preferably sodium hydride, in a suitable solvent for carrying out Process $a^1$ under anhydrous conditions, e.g. at 20° to 30° C. While Compounds IIIa are disclosed as triphenyl compounds it will be appreciated that equivalent radicals, particularly aryl radicals, could be substituted, therefor, without departing from the spirit of this invention. Likewise, while Compounds IIIb are disclosed as diethyl compounds, other alkyl radicals, e.g., having up to 8 carbon atoms, could be substituted therefor, without departing from the spirit of this invention.

In the above presented description of Process $a^1$, Compounds II are referred to as ketene compounds, as it is believed that this is the form in which they react. Such reactants, however, are formed from corresponding acid halides of the formula II'

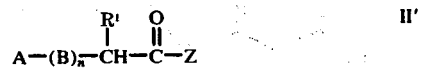

II' wherein A, B, n and $R^1$ are as defined above, and Z is chloro or bromo, by subjection to a base. The base may be a Compound IIIa, present in excess to serve as such base. Thus a Compound II may be formed under the conditions of Process $a^1$ and reacted as it forms. However, if desired, Compounds II may be prepared beforehand by treatment of a Compound II' with a strongly basic amine, e.g., a tri (lower) alkyl amine, such as triethylamine, e.g., at reduced temperature, e.g., from about $-10°$ to 5° C., in an inert solvent such as ether, and the resultant Compound II recovered by conventional means. Compounds II' are known and many are available commercially, or where not known may be prepared by methods analogous to those described in the literature for the preparation of the known compounds, e.g., by halogenation of a corresponding carboxylic acid with thionyl chloride or bromide.

The above described preparation of Compounds I is designated method (a) and may be conveniently represented by reaction Scheme A, below, wherein A, B, $R^1$, $R^2$, $n$, Z and M' are as defined above:

lyzed with water or an aqueous acid or salt, such as dilute hydrochloric acid, or saturated aqueous sodium or ammonium chloride to obtain the desired compound. Compounds IV, i.e., the above-described Grignard reagents, are prepared (Process $b^2$) by treating magnesium with a halo compound of the formula

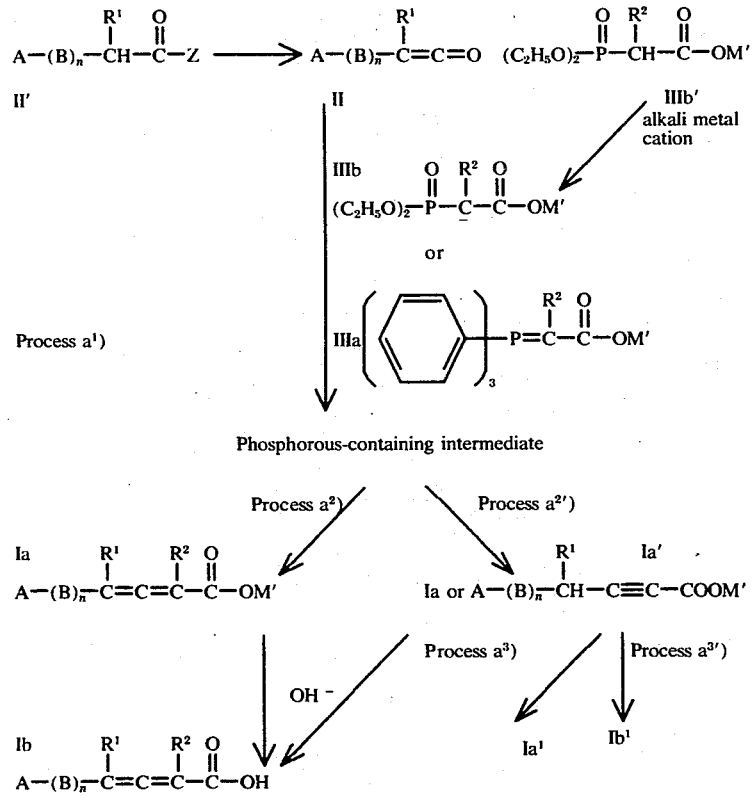

A preferred method preparing Compounds $I^2$, i.e. compounds I, wherein $R^1$ is T-butyl, involves Grignard-caboxylation (Process $b^1$) of a corresponding Grignard reagent, i.e., a Compound IV:

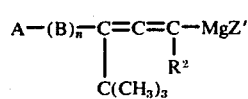
                 IV wherein A, B, $R^2$ and $n$ are defined above, and Z' is chloro or bromo, by reaction with a reagent of formula V

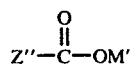
      V wherein M' is as defined above and Z'' is chloro or bromo, to obtain a corresponding Compound Ia; or with carbon dioxide to obtain a corresponding Compound Ib. Process $b^1$ is carried out under conditions conventionally associated with Grignard reactions, i.e., the Grignard reaction is carried out under anhydrous conditions (moisture being excluded from reagents and apparatus), at temperatures of from about 15° to 70° C., preferably at from about 20° to 30° C., in a suitable medium. The resultant Grignard adduct, is then decomposed in the conventional manner, i.e., it is hydro-

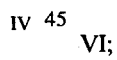
VI;

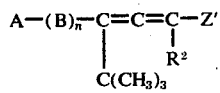
            VI wherein A, B, $n$, $A^2$ and Z' are as defined above, and ethylene dibromide, in the presence of a catalytic amount of mercuric chloride in a suitable medium at a temperature of from about 30° to 70° C., preferably the reflux temperature of the medium, under anhydrous conditions. Suitable mediums referred to in connection with Process $b^1$ and $b^2$ above, are those which are not detrimental to the reaction, generally aprotic organic solvents, e.g., an ether, such as ether (diethyl ether), or tetrahydrofuran.

Compounds VI are known or where not known may be prepared by methods analogous to those described in the literature for the preparation of known compounds. For example, a Compound VI may be obtained by halogenation of an alkynol compound of the formula VII:

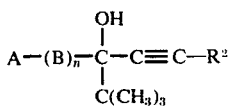   VII wherein A, B, $R^2$ and $n$ are as defined above, with thionyl chloride or bromide, in the conventional manner, e.g., in the presence of pyridine, in ether or tetrahydrofuran at a temperature of from about 0° to 35° C, (Process $b^3$).

A convenient method of preparing Compounds Ia and Ib wherein $R^1$ is alkyl other than tert.-butyl, i.e., a compound of the formula $I^{2'}$

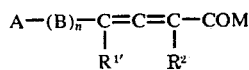   $I2'$ wherein A, B, M, $n$ and $R^2$ are as defined above, and $R^{1'}$ is the same as $R^1$ when it is alkyl other than tert. butyl, may be prepared in an analogous manner to Processes $b^1$ and $b^2$, utilizing a corresponding analog of Compound VI i.e., a Compound VI':

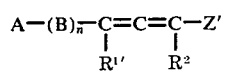   VI' wherein A, B, $n$, $R^{1'}$ and $R^2$ and $Z'$ are as defined above.

Compounds VI' may be prepared, e.g., by reaction of a corresponding alkynol of the formula VII':

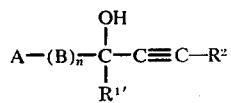   VII' wherein A, B, $n$, $R^{1'}$ and $R^2$ are as defined, with hydrobromic acid/ammonium bromide in the presence of cuprous chloride, at temperatures of about 20° to 30° C., i.e., Process $b^{3'}$).

Compounds VII and VII' are known, or where not known may be prepared by methods analogous to those described in the literature for the preparation of known compounds. For example, Compounds VII or VII' may be obtained by reacting a compound of formula VII:

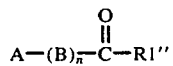   VIII wherein A, B and $n$ are as defined above and $R^{1''}$ is the same as $R^1$ when it is alkyl, with a lithium alkyne of the formula VIIIa:

VIIIa 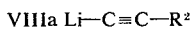

wherein $R^2$ is as defined above, in a solution of an ether, such as diethyl ether or tetrahydrofuran, at a temperature of from about 0° to 35° C. The resultant product (adduct) is hydrolyzed in the general manner of the hydrolysis step of Process $b^1$) above, to give the desired Compound VII or VII'.

Compounds VIII used in the preparation of Compounds VII and VII' are known, some being available commercially, or where not known may be prepared by methods analogous to those described in the literature for the preparation of known compounds; for example, when $n=0$, by preparing a Grignard reagent of a compound of formula VIIIb:

VIIIb  A—Br wherein A is as defined above, and reacting it with a carbonyl compound of the formula VIIIc:

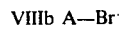   VIIIc where $R^{1''}$ is as defined above, under conventional Grignard conditions, such as are described in the connection with Process $b^1$. When $R^2$ is a hydrogen atom, a convenient form of a Compound VIIIa is lithium acetylide/ethylene diamine complex.

The above-described processes for preparing Compounds $I^2$ by Process $b^1$ and related processes are designated "method $b$" and may be conveniently represented by Reaction Scheme B wherein A, B, $n$, $R^{1'}$, $R^{1''}$, $Z''$, $R^2$, $Z'$ and $M'$ are as defined above, Compounds VII″ = VI + VI′, IV′ is a composite of IV and its $R^{1'}$ analog, and $Ia^{2''}$ and $Ib^{2''}$ are the respective composite ester and acid forms of compounds $I^2$ and $I^{2'}$:

REACTION SCHEME B (Method b)

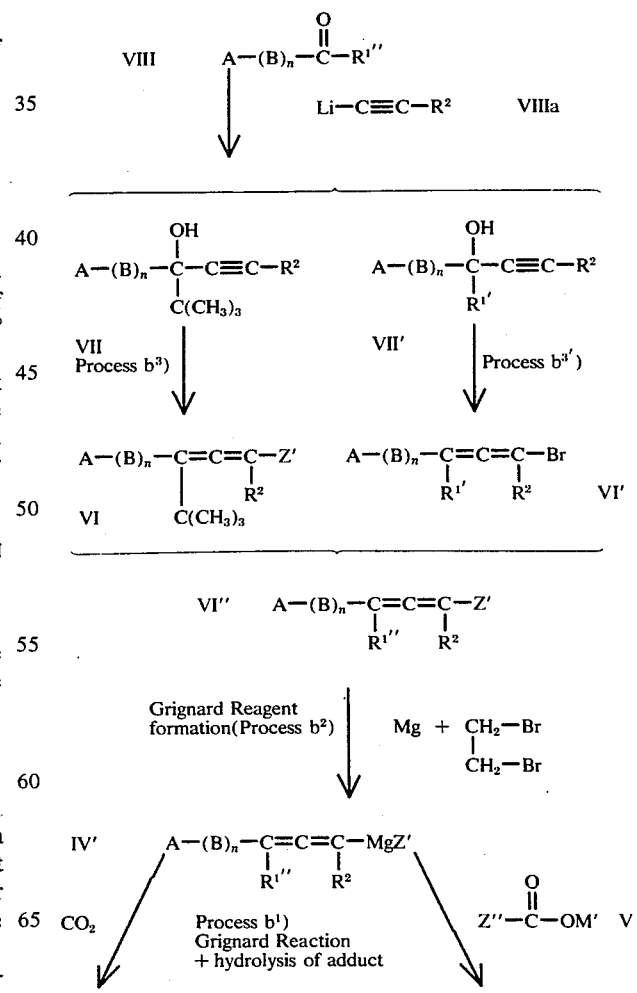

-continued

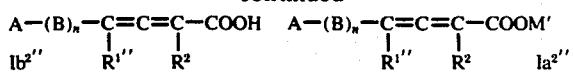

A method of preparing Compounds I'', i.e., Compounds I wherein $R^1$ and $R^2$ are hydrogen, i.e., are other than alkyl, and Y is other than thioalkyl, involves basic rearrangement (Process $c^1$) of a compound of formula IX:

wherein B, M and $n$ are as defined above and A' is the same as A, provided that Y cannot be thioalkyl, Process c1 is carried out by treating a Compound IX in the same manner as described above for Processes $a^3$ and $a^{3'}$; hence, in a suitable solvent with a strong aqueous or non-aqueous inorganic base to obtain the corresponding acid or ester forms, respectively (Ia'' or Ib'').

Compounds IX are known or where not known may be prepared by methods analogous to those described in the literature for the preparation of known compounds. For example, Compounds IX', i.e., Compounds IX where M is a hydrogen atom, may be prepared by oxidation of a corresponding but-3-yn-1-ol of formula X:

wherein A', B and $n$ are as defined above (Process $c^2$). The oxidation is carried out employing chromium trioxide ($CrO_3$) in aqueous sulfuric acid/acetone at low temperature, e.g., from 0° to 10° C.

Where a Compound IX in which M is alkyl (IX'') is desired, such an ester compound can be obtained by esterification of a corresponding Compound IX' by conventional means, e.g., by heating with a alkanol bearing the desired moiety in the presence of an esterification catalyst or other such well known techniques.

Compounds X, in turn, are known or where not known may be prepared by methods analogous to those described in the literature for the preparation of known compounds. For example, Compounds X may be prepared by reaction of ethylene oxide with a Grignard reagent prepared from an acetylenic compound of the formula XI:

XI 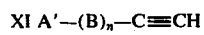

wherein A', B and $n$ are as defined above, in a suitable solvent, e.g., an ether such as tetrahydrofuran or ether, under anhydrous conditions, at moderate temperatures, e.g., from about 0° to 66° C. in process $c^3$. The Grignard reagent for Process $c^3$ may be obtained in the conventional manner, e.g., in the general manner as described above for the preparation of other Grignard reagents, and the Grignard adduct decomposed and the desired product recovered in the manner described above in connection with Grignard reactions.

Compounds XI, in turn, are known, or where not known may be prepared by a method analogous to those described in the literature for the preparation of known compounds.

The preparation of Compounds I'' by the Process $c^1$ and related processes, is conveniently represented by Reaction Scheme C, below wherein A', B, M' and $n$ are as defined above:

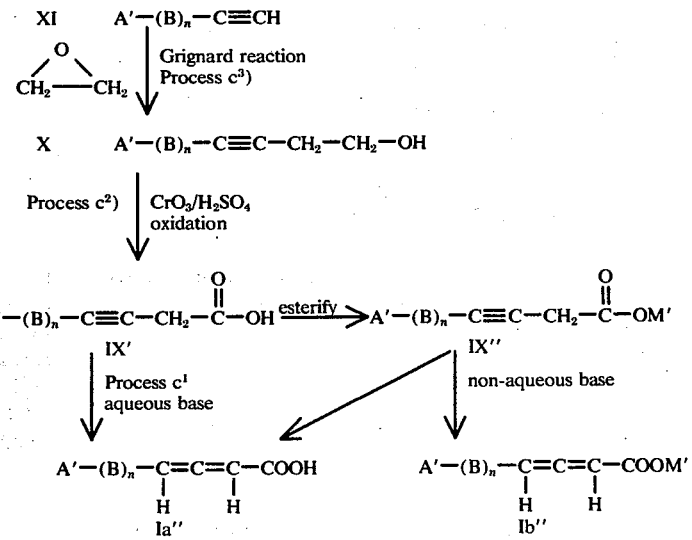

An alternative method of preparing compounds Ib, particularly where A is a phenyl-type radical in which Y is alkoxy or alkylthio having from 5 to 24 carbon atoms, is comprised of a series of reaction steps which may be conveniently represented in Reaction Scheme D, below, in which the substitutents A, B, n, $R^1$ and $R^2$ are as defined above, while Compounds D, E, F and G and processes $d^1$ $d^2$ and $d^3$ are described hereinafter as method d.

REACTION SCHEME D (method d)

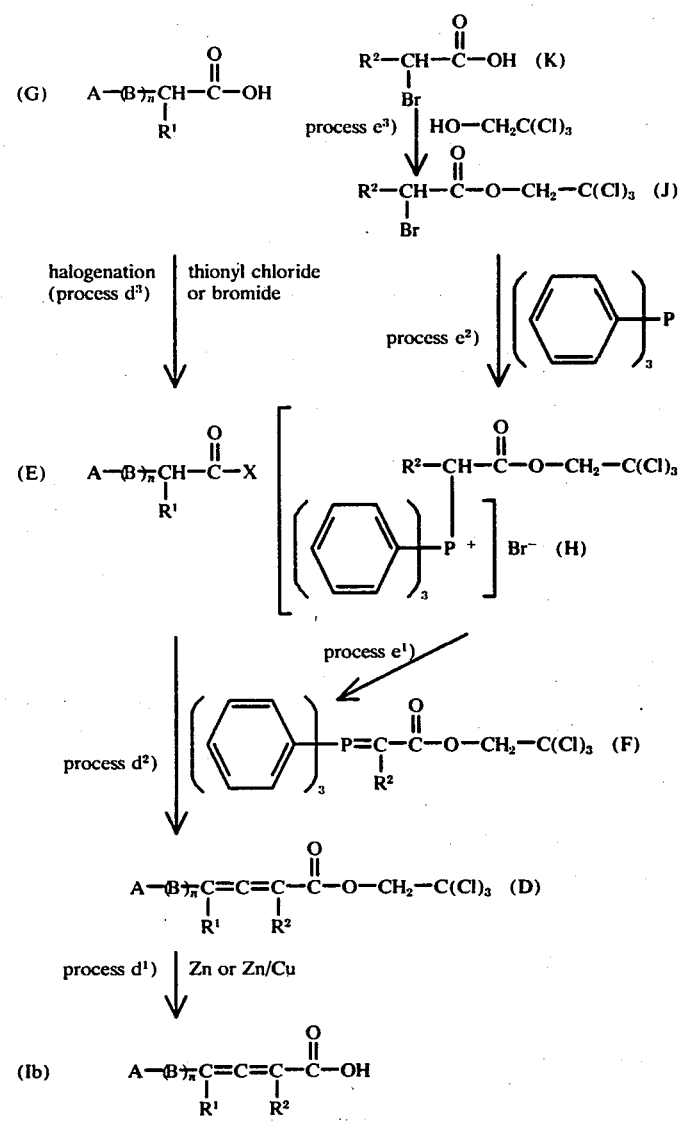

Process d¹ comprises treating a corresponding trichloroethyl ester of the desired Compound I^b, i.e., a compound D:

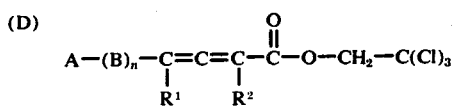

in which A, B, n, R¹ and R² are as defined above, in a suitable reaction medium, in the presence of finely divided zinc or zinc-copper, preferably finely divided zinc-copper, e.g. as dust.

In carrying out process d¹, a suitable reaction medium is one which is inert and serves as a solvent for compounds D, e.g., concentrated aqueous acetic acid when zinc is used and dimethyl formamide when zinc-copper is used. Reaction temperatures are moderate, e.g., those of from about 20° to 35° C. The zinc-copper reagent may be obtained by the procedure described by E. Le Goff in the Journal of Organic Chemistry, 29, 2048 (1964). Essentially anhydrous conditions are employed when zinc-copper is used and are achieved by means conventionally practiced where it is desired to essentially exclude moisture, e.g., by the use of absolute (dry) reaction medium and reagents, employing moisture-free apparatus and excluding moisture-laden air. The concentrated aqueous acetic acid medium has from about 70 to 95% acetic acid, preferably about 90%, (volume/volume).

Compounds D, described above, are obtainable by reaction of an acyl halide of formula E:

(E)  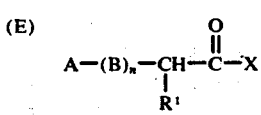

in which A, B, n and R¹ are as defined above, and X is halo having an atomic weight from about 34 to 80, preferably chloro, with a, β, β, β-trichloroethyl phosphorous ester of the formula F:

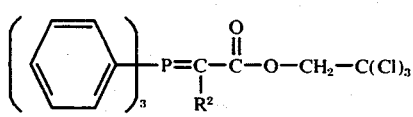

in which R² is as defined above, in a solvent under essentially anhydrous conditions (process d²).

Process d² may be conventionally carried out in an inert organic solvent, such as a cyclic ether, e.g., tetrahydrofuran, and at an elevated temperature, e.g., from about 50° to 100° C, preferably at the reflux temperature of the reaction mixture. Essentially, anhydrous conditions may be achieved in the manner described above with respect to process d¹.

Compounds E are known and may be prepared by methods described in the literature, or where not known may be attained by methods described in the literature for the preparation of known compounds, e.g., by halogenation of corresponding carboxylic acid forms, i.e., compounds of formula G (process d³):

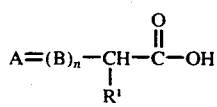

in which A, B, $n$ and R¹ are as defined above.

Process d³ may be carried out in the conventional manner for the conversion of a carboxylic acid to its acyl halide, e.g., by treatment with thionyl chloride or thionyl bromide (depending upon whether it is desired that X be chloro or bromo) at elevated temperatures, e.g., from about 50° to 160° C, preferably at the reflux temperature of the reaction mixture under essentially anhydrous conditions. An inert solvent such as an aromatic solvent, e.g., benzene, toluene or xylene, may be used, or the halogenating agent may be employed in large excess to serve as solvent.

The trichloroethyl ester reactants (Compounds F) used in process d¹, above, are obtainable by a series of reaction steps starting with the reaction of β,β,β-trichloroethanol with an α-R², α-bromo-substituted acetic acid (i.e., a compound of formula K), (process e³), to obtain a corresponding trichloroethanol ester of the particular α-bromo alkanoic acid, i.e., a compound J; which is then reacted (process e²) with triphenylphosphine to obtain a phosphoryl bromide compound (compound H) which is then reacted (process e¹) with an aqueous solution of an alkali metal hydroxide to obtain the desired compound F, as is shown in Reaction Scheme D, above.

The above-described esterification, (process e³), is carried out in the conventional manner, e.g. under strongly acidic conditions, which may be provided by the inclusion of a mineral acid, preferably concentrated sulfuric acid, in the presence of an inert solvent, particularly one which forms an azeotrope with water, e.g., an aromatic solvent, such as benzene, toluene or xylene, preferably toluene, at temperatures of e.g., from about 80° to 160° C. preferably at the reflux temperature of the reaction mixture, under conditions in which water formed in the reaction is removed from the reaction zone, preferably by employing a Dean-Stark trap.

Process e², the condensation of a resulting α-bromo acetic acid ester with triphenylphosphine may be carried out in the presence of an inert solvent, e.g., an aromatic solvent such as benzene, toluene or xylene, preferably benzene, at a temperature of from about 60° to 140° C., e.g. at the reflux temperature of the reaction mixture, under essentially anhydrous conditions.

Process e¹ is carried out under dehydrohalogenating conditions by treating the desired phosphoryl compound (a compound H) with an aqueous solution of an alkali metal hydroxide, such as sodium hydroxide or potassium hydroxide, preferably sodium hydroxide (at e.g. about 5 to 15% w/v concentration), preferably in the presence of an inert solvent such as methylene chloride, at moderate temperatures, e.g., from about 15° to 50° C., e.g. at room temperature.

Other above-described starting materials and reagents, e.g., Compounds G and K are known, and are obtainable by methods described in the literature; some being commercially available, or where not known, may be prepared by methods analogous to those described in the literature for the preparation of those compounds which are known. It will be noted that compounds II' of method a are equivalent to compounds E of method d.

The above-described final compounds and intermediates may be recovered and refined by conventional techniques, e.g., by crystallization, distillation or chromatographic techniques, e.g., thin-layer or column chromatography, as is appropriate.

The compounds of formula I are useful because they possess pharmacological activity in mammals. In particular, the Compounds I are useful as anti-inflammatory agents and as hypolipidemic agents.

The activity of Compounds I aas anti-inflammatory agents is indicated by the Carrageenan induced edema test on rats (oral administration at 10 to 200 mg/kg). For such use, the compounds may be combined with a pharmaceutically acceptable carrier, and such other conventional adjuvants as may be necessary, and administered orally in such forms as tablets and capsules, elixirs, suspensions and the like or parenterally in the form of an injectable solution or suspension. The dosage administered will, of course, vary depending upon the compounds used and mode of administration. However, in general, satisfactory results are obtained when administered at a daily dosage of from about 1 mg to about 250 mg per kilogram, e.g., from about 1 mg to about 175 mg per kg of body weight, preferably given in divided doses 2 to 4 times a day, or in sustained release form. For most mammals, the administration of from about 100 mg to about 3000 mg, e.g., from about 160 mg to about 2000 mg, of the compound per day provides satisfactory results and dosage forms suitable for internal administration comprise from about 25 mg to about 1500 mg, e.g., from about 40 mg to about 1000 mg, of the compound in admixture with a solid or liquid pharmaceutical carrier or diluent.

The activity of compounds I as hypolipidemic agents, particularly hypolipoproteinemia agents, is evidenced, for example, by lowering cholesterol and triglyceride blood serum levels in tests on a group of white rats which are given typically 10 to 50 milligrams per kilogram of body weight per diem of the compound orally, for 6 days, followed by extraction wit isopropanol of serum or plasma after anesthetizing the rats with sodium hexobarbital, and then noting the cholesterol and triglyceride contents as compared to those of a control group. The cholesterol and triglyceride contents are determined by the methods described by Lofland, H.B., Anal. Biochem. 9:393 (1964) : (Technicon method N 24a) : and G. Kessler and H. Lederer, Technicon Symposium, Mediad Inc., New York, pgs. 345-347 (1956), respectively. For such usage, the compounds may be administered orally or parenterally, preferably orally, and in admixture with conventional pharmaceutical carriers. The dosage administered may vary depending upon known variables such as the particular compound employed and the severity of the condition being treated. In general, satisfactory results are obtained when administered at a daily dosage of from about 1 milligram to about 250 milligrams per kilogram of animal body weight, preferably given orally and in divided doses, 2 to 4 times a day, or in sustained release form. For most mammals the total daily dosage is from about 50 milligrams to about 2000 milligrams of the compound, and dosage forms suitable for internal administration comprise from about 12.5 to 1000 milligrams of the compound in admixture with a solid or liquid pharmaceutically acceptable carrier or diluent.

For above uses, compounds I may be administered orally in such forms as tablets, dispersible powders, granules, capsules, syrups and elixirs; and parenterally as solutions, suspensions, dispersions, emulsions, and the like, e.g. a sterile injectable solution such as an aqueous suspension. These pharmaceutical compositions may contain from about 0.5% up to about 90% of the active ingredient in combination with the carrier or adjuvant, more usually between 4% and 60% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g. inert diluents such as calcium phosphate, calcium sulphate dihydrate, lactose and talc, granulating and disintegrating agents, e.g. starch and alginic acid, binding agents, e.g. starch, gelatin, polyvinyl pyrrolidone and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g. calcium carbonate, calcium phosphate, kaolin, polyoxyethylene glycol, peanut oil, sesame oil and corn oil.

Convenient unit dosage forms for the above-described uses are those having from about 12.5 to 1500 mg., preferably about 12.5 to 500 mg. of a compound I as active ingredient. The preferred pharmaceutical compositions from the standpoint of preparation and ease of administration are solid orally administrable compositions, particularly tablets and solid or liquid diluent-filled capsules (as appropriate to the nature of the particular active ingredient), containing, e.g. from about 12.5 to 500 mg. of the active ingredient.

The compounds Ib, i.e. compounds I in which M is a hydrogen atom, form salts and the pharmaceutically acceptable salts thereof are included within the scope of the pharmaceutically useful compounds of the present invention. Such salts are the pharmaceutical equivalents of their acid forms, and include, by way of illustration, the sodium salt and the triethyl ammonium salt. In general, the salts may be produced from the free acids by established procedures. Conversely, the free acids may be obtained from the salts by well-known procedures. It will be appreciated that while the Compounds Ib are generally referred to in the processes herein described as acid forms, they may actually be present in the form of their corresponding salts under particular reaction conditions, and may be recovered directly in pharmaceutically acceptable salt form, by conventional methods.

Capsules and tablets containing the ingredients indicated below may be prepared by conventional techniques and are useful in treating inflammation or lipidemia, particularly hyperlipoproteinemia, in mammals at a dose of one capsule or tablet two to four times per day:

| Ingredient | Weight in Milligrams | | |
|---|---|---|---|
| | Tablet | Capsule | Capsule |
| 4-(p-tetradecyloxyphenyl)-2-methyl-buta-2,3-dienoic acid | 50 | 50 | 30 |
| Tragacanth | 10 | | |
| Lactose | 197.5 | 170 | |
| Corn Starch | 25 | | |
| Talcum | 15 | | |
| Magnesium Stearate | 2.5 | | |
| Polyethylene Glycol (M.W. 6000) | | | 300 |

In the following examples, which are illustrative of the invention, temperatures are in degrees centigrade, and room temperature is 20° to 30° C., unless indicated otherwise.

EXAMPLE 1

Ethyl 4-(p-thiomethylphenyl)-2-methyl-buta-2,3-dienoate

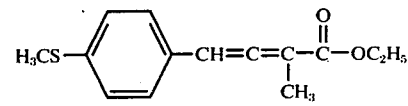

Step A p-thiomethylphenyl acetyl chloride

A solution of 9.4 g of p-thiomethylphenyl acetic acid in 280 ml of benzene is treated with 28 ml of thionyl chloride and stirred at room temperature for 16 hours. The reaction mixture is evaporated under vacuum (i.v.) and aziotroped several times with benzene to remove residual thionyl chloride, to obtain p-thiomethylphenyl acetyl chloride, which may be used in Step B, below, without further refining.

Step B Ethyl 4-(p-thiomethylphenyl)-2-methyl-buta-2,3-dienoate

To a solution of 36.0 g of carbethoxyethylidene-triphenylphosphorane in 200 ml of absolute tetrahydrofuran (THF), is added 8.0 g of p-thiomethylphenyl acetyl chloride in 40 ml of abs. THF. The mixture is then refluxed for 4 hours and then stirred for 16 hours at room temperature. The reaction mixture if filtered, and the filtrate evaporated i.v. to obtain crude title product, which may be further refined or used as such in Example 2.

EXAMPLE 2

4-(p-thiomethylphenyl)-2-methyl-buta-2,3-dienoic acid 31.4 g of the crude ester obtained in Example 1 is dissolved in 100 ml of ethanol. To the solution is added a solution of 3.0 g sodium hydroxide in 50 ml of distilled water. The resultant mixture is stirred for 6 hours at room temperature. The ethanol is substantially removed by evaporation i.v. and the residue acidified with 2N hydrochloric acid. The acidified mixture is extracted 3 times with 30 ml portions of ether. The combined ether extracts are washed with water, and then dried over anhydrous sodium sulfate (S.S.), which is then removed by filtration, and the filtrate evaporated i.v. to dryness to obtain a residue which is refined by crystallization from ether to obtain the title compound, m.p. 138° – 142°.

EXAMPLE 3

Repeating the procedure of Example 1 but replacing the p-thiomethylphenyl acetyl chloride with an equivalent amount of p-methoxyphenyl acetyl chloride, there is similarly obtained ethyl 4-(p-methoxyphenyl)-2-methyl-buta-2,3-dienoate, which when treated according to the procedure of Example 2, yields 4-(p-methoxyphenyl)-2-methyl-buta-2,3-dienoic acid (m.p. 105° – 108° from ether/pentane).

EXAMPLE 4

4-(p-chlorophenyl)-penta-2,3-dienoic acid

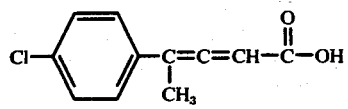

Step A Intermediate

A solution of 2.03 g of 2-(p-chlorophenyl) propionyl chloride in 10 ml benzene is added to a stirred suspension of 6.7 g of (carbethoxymethylene)-triphenylphosphorane in 50 ml benzene. The mixture is stirred at 22° for 3 hours then filtered, and the filtrate evaporated to obtain an intermediate, p-chlorophenylpropionyl-triphenylphosphin-carbethoxymethylene (m.p. 120° – 122° from ether acetate/hexane).

Step B 4-(p-chlorophenyl)-penta-2,3-dienoic acid

The intermediate obtained in Step A is subjected to short path distillative pyrolysis (240° to 260°/0.1 mm Hg). The distillate is taken up in hexane and the triphenylphosphinoxide side-product filtered off. The filtrate is evaporated (removing the hexane) to obtain an oily residue. The residue is dissolved in 30 volumes of methanol mixed with 3 volumes of 40% aqueous sodium hydroxide and kept at 20° for 48 hours. 30 volumes water are then added, and the mixture concentrated by removing most of the methanol by evaporation. The aqueous residue is filtered, and then acidified (to PH₂) with concentrated hydrochloric acid. The title acid precipitates, is recovered and refined by crystallization from methanol/water, m.p. 146°–148°.

EXAMPLE 5

5-(p-chlorophenyl)-5-methyl-hexa-2,3-dienoic acid

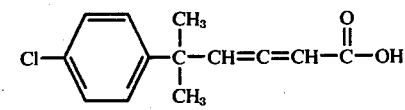

Step A Intermediate

Following the procedure of Step A of Example 4, but using an approproximately equivalent amount of 3-(p-chlorophenyl)-3-methyl-butyryl chloride, in place of the 2-(p-chlorophenyl)-propionyl chloride used therein, there is similarly obtained the corresponding intermediate, m.p. 133° – 137.5°, crystallized from methanol/methylene chloride.

Step B ethyl 5-(p-chlorophenyl)-5-methyl-2-hexynoate

Repeating the procedure of Step B of Example 4, using the intermediate of Step A of this example (pyrolysis at 220° – 250°/0.2 mm Hg) yields an oil (b.p. 144° – 146° at 0.6 mm Hg) of the structure of ethyl 5-(p-chlorophenyl)-5-methyl-2-hexynoate.

Step C 5-(p-chlorophenyl)-5-methyl-hexa-2,3-dienoic acid 16 g of the product of Step B is dissolved in a minimum amount of ethanol and the solution added to 96 ml of 20% aqueous sodium hydroxide. Under a nitrogen atmosphere, the mixture is heated to 110° for 6 hours while permitting most of the ethanol to distill off. After cooling, the mixture is acidified to PH₂ with conc. hydrochloric acid, the title product recovered by filtration, and refined by crystallization from petroleum ether, m.p. 64° – 67°.

EXAMPLE 6

Ethyl 4-(6-methoxy-2-maphthyl)-penta-2,3-dienoate

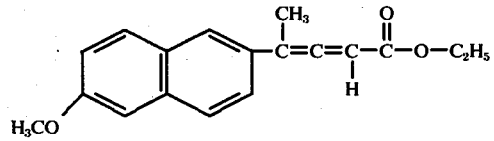

To a solution of 74.6 g of 6'-methoxy-2'-naphthyl-2-propionyl chloride in 300 ml of ether, is slowly added, at −5°, 39.0 ml of triethylamine. After stirring for 3 hours, the resultant triethylamine hydrochloride is removed by filtering, and the filtrate evaporated to dryness to obtain a residue. The residue is taken up in 200 ml of dry 1,2-dimethoxyethane and added, dropwise, to a refluxing mixture prepared from 35.4 g of tri-ethylphosphonoacetate*, 7.6 g of 50% sodium hydride/paraffin and 730 ml. of 1,2-dimethoxyethane. After addition is completed, the mixture is refluxed for 30 minutes. The mixture is then cooled to 5°, poured into 2 liters of 1% aqueous potassium bicarbonate solution, and extracted with benzene. The benzene extracts are combined, dried over anh. S.S. and evaporated to give crude title product as a residue which is refined by crystallization from ethyl acetate/hexane (1:1). m.p. 112°–114°.

* which may also be designated diethyl ethoxycarbonylmethylphosphonate

EXAMPLE 7

5-(p-fluorophenyl)-2,5-dimethyl-hexa-2,3-dienoic acid

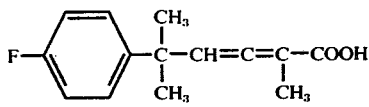

Repeating the procedure of Example 1, step B, but replacing the p-thiomethylphenyl)-acetyl chloride, used therein, with an approximately equivalent amount of 3-(p-fluorophenyl)-3-methyl-butyryl chloride, there is accordingly obtained ethyl 5-(p-fluorophenyl)-2,5-dimethyl-hexa-2,3-dienoate, which upon treatment according to Example 2, yields 5-(p-fluorophenyl)-2,5-dimethyl-hexa-2,3-dienoic acid, m.p. (72.5° – 75.5°).

EXAMPLE 8

Repeating the procedure of Example 7, but replacing the 3-(p-fluorophenyl)-3-methyl-butyryl chloride used therein with an approximately equivalent amount of 3-(p-chlorophenyl)-3-methyl-butyryl chloride, there is accordingly obtained ethyl 5-(p-chlorophenyl)-2,5-dimethyl-hexa-2,3-dienoate from which is obtained 5-(p-chlorophenyl)-2,5-dimethyl-hexa-2,3-dienoic acid (m.p. 106° – 107.5°).

EXAMPLE 9

Step A:
Repeating the procedure of Example 1, Step B, but replacing the p-thiomethylphenyl acetyl chloride used therein with an approximately equivalent amount of:
a) p-chlorophenyl acetyl chloride;
b) m-chlorophenyl acetyl chloride;
c) 2-(p-chlorophenyl) propionyl chloride;
d) 2,4-dichlorophenyl acetyl chloride;
e) 2,6-dichlorophenyl acetyl chloride;
f) p-biphenylyl acetyl chloride;
g) 2-(6'-methoxy-2'-naphthyl) propionyl chloride;
h) (6'-methoxy-2'-naphthyl) acetyl chloride;
i) 4'-benzothienyl acetyl chloride*
j) p-ethyl-phenyl acetyl chloride
there is accordingly obtained:
a) ethyl 4-(p-chlorophenyl)-2-methyl-buta-2,3-dienoate;
b) ethyl 4-(m-chlorophenyl)-2-methyl-buta-2,3-dienoate;
c) ethyl 4-(p-chlorophenyl)-2-methyl-penta-2,3-dienoate;
d) ethyl 4-(2,4-dichlorophenyl)-2-methyl-buta-2,3-dienoate;
e) ethyl 4-(2,6-dichlorophenyl)-2-methyl-buta-2,3-dienoate;
f) ethyl 4-(p-biphenylyl)-2-methyl-buta-2,3-dienoate;
g) ethyl 4-(6'-methoxy-2'-naphthyl)-2-methyl-penta-2,3-dienoate;
h) ethyl 4-(6'-methoxy-2'-naphthyl)-2-methyl-buta-2,3-dienoate;
i) ethyl 2-methyl-4-(4'-benzothienyl)-buta-2,3-dienoate; or
j) ethyl 4-(p-ethyl-phenyl)-2-methyl-buta-2,3-dienoate;

* The benzothienyl radical is also known as benzothiofuranyl or thionaphthyl.

Step B:
Treatment of the ester products obtained by step A according to the procedure of Example 2, yields the following acid products, respectively;
a) 4-(p-chlorophenyl)-2-methyl-buta-2,3-dienoic acid, (m.p. 130° – 132°);
b) 4-(m-chlorophenyl)-2-methyl-buta-2,3-dienoic acid, (m.p. 100° – 101°);
c) 4-(p-chlorophenyl)-2-methyl-penta-2,3-dienoic acid, (m.p. 161° – 162°);
d) 4-(2,4-dichlorophenyl)-2-methyl-buta-2,3-dienoic acid, (m.p. 135.5° – 136.5°);
e) 4-(2,6-dichlorophenyl)-2-methyl-buta-2,3-dienoic acid;
f) 4-(p-biphenylyl)-2-methyl-buta-2,3-dienoic acid;
g) 4-(6'-methoxy-2'-naphthyl)-2-methyl-penta-2,3-dienoic acid;
h) 4-(6'-methoxy-2'-naphthyl)-2-methyl-buta-2,3-dienoic acid;
i) 2-methyl-4-(4'-benzothienyl)-buta-2,3-dienoic acid; or
j) 4-(p-ethyl-phenyl)-2-methyl-buta-2,3-dienoic acid.

EXAMPLE 10

4-BIPHENYLYL-5,5-DIMETHYL-HEXA-2,3-DIENOIC ACID

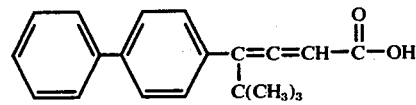

Step A 4-phenylpivalophenone

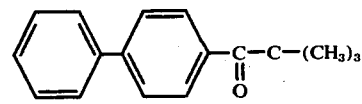

To a 2 liter, 4 necked flask, equipped with a stirrer, thermometer, condenser and a dropping funnel is added 13.4 g of magnesium turnings and a small crystal of iodine. The flask is warmed to vaporize the iodine, and to the warmed flask, is added in one portion 30 g of 4-bromobiphenyl in 100 ml of absolute THF, resulting in a vigorous, but controlable reaction. 86 g of 4-bromo-biphenyl in 290 ml of absolute THF is added at a rate so as to maintain the reaction at gentle reflux. After the addition is completed, the mixture is refluxed for 45 minutes (resulting in the formation of a Grignard reagent). The thus prepared Grignard agent is transferred to a dropping funnel (under dry nitrogen gas), and slowly added to a mixture of 70 g of trimethyl acetyl chloride in 200 ml of THF. After addition is completed, the mixture is stirred for 1 hour at room temperature. The mixture is then decomposed by dropwise addition of 500 ml of 2N hydrochloric acid. 200 ml of brine (saturated aqueous sodium chloride) is then added with 200 ml. ether and the organic phase separated. The organic phase is washed 3 times with 2N sodium carbonate, dried over anh. S.S., filtered and the filtrate evaporated (i.v.) to obtain a residue, from which is obtained 4-phenylpivalophenone, m.p. 94° – 96° C. from ether.

Step B 3-biphenylyl-4,4-dimethyl-pent-1-yn-3-ol

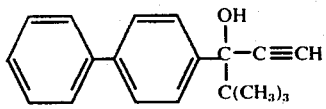

To a saturated solution of acetylene in 1500 ml of abs. THF is added 77 g of lithium acetylide/ethylenediamine complex. A solution of 80g. of 4-phenylpivalophenone in 400 ml. THF is added dropwise over a period of 30 minutes, during which time acetylene is bubbled through the reaction mixture. After stirring for one hour at room temperature, the reaction mixture is decomposed by dropwise addition of 500 ml. of water. 200 ml. of brine and 200 ml of ethyl acetate are then added to the reaction mixture. The organic phase is separated, washed 3 times with 100 ml. portions of distilled water, dried over anh. S.S., filtered and evaporated (i.v.) to dryness to obtain a residue. From the residue is obtained 3-biphenylyl-4,4-dimethyl-pent-1-yn-3-ol, m.p. 154° – 155° C., by crystallization from ether/pentane.

Step C  1-chloro-3-biphenylyl-4,4-dimethyl-1,2-pentadiene

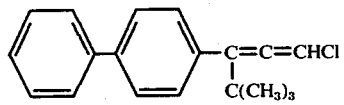

To a solution of 26.5 g of 3-biphenylyl-4,4-dimethyl-pent-1-yn-3-ol in 150 ml of abs. THF at 0° – 5° is added 8.0 g of pyridine. A solution of 12.5 g of thionyl chloride in 15 ml of abs. THF is then added dropwise over a period of 30 minutes. The reaction mixture is then stirred at room temperature for 4 hours and the precipitate that forms filtered off. The filtrate is diluted with 200 ml ether and the organic phase washed three times with 2N hydrochloric acid, then with distilled water, dried over anh. S.S., filtered and evaporated i.v. to obtain a residue.

The residue is chromatographed on silica gel using chloroform/pentane (1:1) as eluent. Upon removal of the solvent (by evaporation) there is obtained 20.4 g of 1-chloro-3-biphenylyl-4,4-dimethyl-1,2-pentadiene (m.p. 85° – 86°).

Step D  4-biphenylyl-5,5-dimethyl-hexa-2,3-dienoic acid

To a suspension of 1.20 g of magnesium turnings and 0.01 g mercuric chloride in 10 ml of abs., THF is added dropwise a solution of 5.6 g of 1-chloro-3-biphenylyl-4,4-dimethyl-1.2-pentadiene and 2.8 g. of ethylenedibromide in 50 ml of abs. THF at such a rate that a gentle reflux is maintained. After addition is completed, the mixture is refluxed for 15 minutes. The reaction mixture is then cooled to room temperature and carbon dioxide gas is bubbled through the reaction mixture for 2.5 hours. The reaction mixture is then decomposed by adding 50 ml of 2N hydrochloric acid, diluted with 200 ml of ether, the organic phase separated, washed 3 times with water, dried over anh. S.S., filtered and evaporated (i.v.) to dryness to obtain a residue, from which title product is crystallized (m.p. 152° – 155°) from pentane.

Repeating the procedure of the example, utilizing appropriate starting materials, there is similarly obtained:
a) 4-(p-fluorophenyl)-5,5-dimethyl-hexa-2,3-dienoic acid (m.p. 96° – 98° from pentane);
b) 4-(p-phenoxyphenyl)-5,5-dimethyl-hexa-2,3-dienoic acid, (m.p. 96° – 98° from pentane);
c) 4-(p-cyclohexylphenyl)-5,5-dimethyl hexa-2,3-dienoic acid (m.p. 133° – 135° from pentane);
d) 4-(m-chloro-p-cyclohexylphenyl)-5,5-dimethyl-hexa-2,3-dienoic acid (m.p. 66° – 70° from pentane);
e) 4-(m-chloro-p-propoxyphenyl)-5,5-dimethyl-hexa-2,3-dienoic acid (sodium salt; m.p. 266° – 269° from pentane); and
f) 4-(p-thiomethylphenyl)-5,5-dimethyl-hexa-2,3-dienoic acid (m.p. 90° – 92° from pentane).
g) 4-(6'-methoxy-2'-naphthyl)-5,5-dimethyl-hexa-2,3-dienoic acid (m.p. 154° – 156°).

EXAMPLE 11

4-(p-biphenylyl)-penta-2,3-dienoic acid

Step A 1-bromo-3-(p-biphenylyl)-1,2-butadiene

A suspension of 1.1 g of 3-(p-biphenylyl)-but-1-yn-3-ol (obtainable analogously to Steps A and B, Example 10), 1.8 g of ammonium bromide and 0.2 g cuprous chloride in 10 ml of 48% hydrobromic acid is stirred for 4 hours at room temperature. The reaction mixture is then poured into water and extracted 3 times with 8 ml portions of methylene chloride. The combined organic extracts are washed 3 times with water, dried over anh. S.S., filtered and evaporated (i.v.) to dryness to obtain a residue. The residue is chromatographed on silica gel using chloroform/pentane (1:1) as eluent. The solvent is removed by evaporation to obtain a residue, from which 1-bromo-3-(p-biphenylyl)-1,2-butadiene is crystallized from pentane.

Step B 4-(p-biphenylyl)-penta-2,3-dienoic acid

Repeating the procedure of Step D of Example 10, but replacing the 1-chloro-3-(p-biphenylyl)-4,4-dimethyl-1,2-pentadiene used therein with an equivalent amount of the product of Step A, there is accordingly obtained the title product of this example.

Following the procedures of this example, using appropriate starting materials, these may similarly be obtained:
a) 4-(p-chlorophenyl)-2-methyl-penta-2,3-dienoic acid, or
b) 4-(6'-methoxy-2'-naphthyl)-2-methyl-penta-2,3-dienoic acid.

EXAMPLE 12

4-(o-cyclohexylphenyl)-buta-2,3-dienoic acid

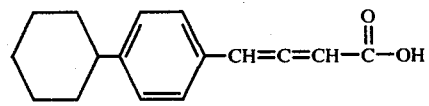

Step A 4-(p-cyclohexylphenyl)-3-butyn-1-ol

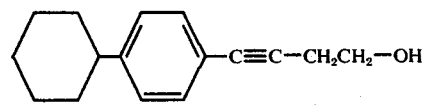

To a solution of 153 g of ethylbromide in 160 ml of abs. THF, is added a suspension of 36 g magnesium turning in 330 ml of THF, (to obtain a solution of ethyl magnesium bromide) and the reaction mixture cooled to 0° to 5°. To the reaction mixture is then added, dropwise, a solution of 214 g of p-cyclohexylphenylacetylene in 420 ml of abs. THF, over a period of one hour. The resulting thick suspension is diluted with 200 of abs. THF and then refluxed for 1.5 hours. The reaction mixture is then cooled to 0°, and a solution of 62 g ethylene oxide in 420 ml of abs. THF added thereto, dropwise, over a period of one hour. After addition is completed, the reaction mixture is refluxed for 2.5 hours, then decomposed by adding dilute sulfuric acid (5%), and extracted with ether. The combined ether extracts are washed with water, then brine, and evaporated i.v. to dryness to obtain a residue from which is crystallized 4-(p-cyclohexylphenyl)-3-butyn-1-ol, m.p. 56° – 59° from pentane.

Step B 4-(p-cyclohexylphenyl)-butyn-3-oic acid

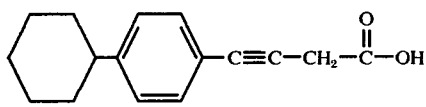

To a solution of 45.6 g of 4-(p-cyclohexylphenyl)-3-butyn-1-ol in 1.1 liter of acetone at 0° to 5° is added dropwise over a period of 45 minutes, 200 ml of a solution of CrO₃ in sulfuric acid (prepared by dissolving 45 g of CrO₃ in 50 ml of conc. sulfuric acid and diluting to 210 ml with distilled water). The reaction mixture is stirred at 5° for 2.5 hours, then diluted with ether and extracted 3 time with ether. The combined ether portions are washed three times with water, then brine, and then dried over anh. SS., filtered and the filtrate evaporated i.v. to dryness to obtain a residue from which is crystallized 4-(p-cyclohexylphenyl)-butyn-3-oic acid, m.p. 128° – 130°, from heptane.

Step C 4-(p-cyclohexylphenyl)-buta-2,3-dienoic acid

A solution of 12.0 g of 4-(p-cyclohexylphenyl)-butyn-3-oic acid in 1200 ml of 2N sodium hydroxide is treated with 50 ml of ethanol and stirred at room temperature for 16 hours. Ethanol is substantially removed from the reaction mixture by evaporation i.v. and the sodium salt of the title compound precipitated, and is filtered off. The precipitate is suspended in water, covered with ether and acidified with 2N hydrochloric acid, with vigorous stirring. The ether layer is then separated, washed with water, dried over anh. S.S., filtered and evaporated i.v. to dryness to obtain the title compound, which is refined by crystallizing from pentane, m.p. 126° – 129°.

Following the procedure of this example, but replacing the p-cyclohexylphenylacetylene used in Step A, with an approximately equivalent amount of:
a) (p-biphenylyl)acetylene;
b) (p-isobutylphenyl)acetylene; or
c) (6'-methoxy-2'-naphthyl)acetylene,
there is accordingly obtained
a) 4-(p-biphenylyl)-buta-2,3-dienoic acid (decomposes at 165°);
b) 4-(p-isobutylphenyl)-buta-2,3-dienoic acid (sodium salt decomposes at 240°); or
c) 4-(6'-methoxy-2'-naphthyl)-buta-2,3-dienoic acid (decomposes at 163°–168°).

EXAMPLE 13

4-(p-Tetradecyloxyphenyl)-2-methyl-buta-2,3-dienoic acid

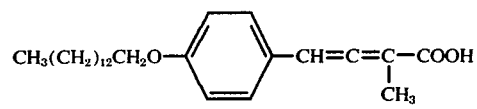

Step A Preparation of β,β,β-Trichloroethyl-2-bromopropionate

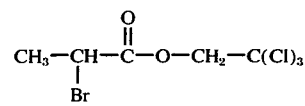

To a solution of 500 g. of 2-bromopropionic acid and 488.5 g. 2,2,2-trichloroethanol in 1000 ml. dry toluene is added 1.5 ml. concentrated sulphuric acid. The reaction mixture is then refluxed with a Dean-Stark trap for 4 hours. After cooling, the organic phase is washed three times with 10% aqueous sodium bicarbonate (weight / volume) solution, then with distilled water, dried over anhydrous sodium sulfate, filtered and solvent removed i.v. to give crude bromo-propionate ester, which is used as such in Step B, below.

STEP B Preparation of β,β,β-trichloroethyl-2-(triphenylphosphoryl)-propionate bromide.

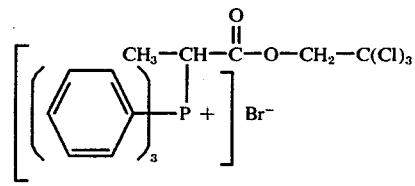

A mixture of 469 g. β,β,β-trichloroethyl-2-bromopropionate and 432.5 g. triphenylphosphine in 1200 ml. dry benzene is refluxed for 16 hours and then cooled. The resultant crystalline title phosphoryl product is filtered off and washed with petroleum ether and dried to give the title phosphoryl product (m.p. 195°–200°).

STEP C Preparation of β,β,β-trichloroethyl-2-(triphenylphosphoranylidene)-propionate.

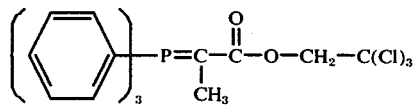

To a solution of 259.5 g. β,β,β-trichloroethyl-2-(triphenylphosphoryl)-propionate bromide in 2000 ml. methylene chloride is slowly added with vigorous stirring a solution of 22 g. sodium hydroxide in 200 ml. water until the pH of the aqueous layer is brought to 7.5. The reaction mixture is then stirred vigorously for a few more minutes. The organic phase is then washed well with water, dried over anhydrous sodium sulfate, filtered and solvent removed i.v. From the resulting residue is crystallized from ethyl acetate/petroleum ether (10:1), the title triphosphoranylidene product (m.p. 155°–160°).

Step D: p-Tetradecyloxyphenylacetylchloride

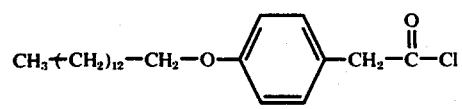

A solution of 10.0 g. p-tetradecyloxyphenylacetic acid in 100 ml. absolute benzene is treated with 19.9 g thionylchloride and refluxed for 2.5 hours. The reaction mixture is then evaporated under vacuum (i.v.) and azeotroped several times with benzene to remove residual thionylchloride, to obtain crude p-tetradecyloxyphenylacetylchloride, which may be used in Step E, below, without further refining.

Step E: $\beta,\beta,\beta$-Trichloroethyl-4-(p-tetradecyloxyphenyl)-2-methyl-buta-2,3-dienoate.

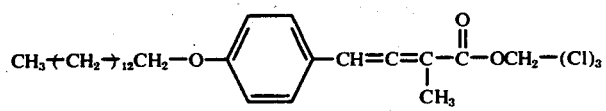

To a solution of 29.3 g. $\beta,\beta,\beta$-trichloroethyl-2-(triphenylphosphoranylidene)-propionate in 150 ml. absolute tetrahydrofurane (THF) is added 10.0 g. of p-tetradecyloxyphenyl-acetylchloride (obtained by Step A, above, in 50 ml. of absolute tetrahydrofurane. The reaction mixture is refluxed for 45 minutes, cooled in an ice bath, filtered and the filtrate evaporated i.v. The residue is triturated with petroether, the undesired solids thus obtained are filtered off and the filtrate is once again evaporated i.v. The residue is dissolved in methylene chloride and filtered rapidly through silica gel to obtain crude $\beta,\beta,\beta$-trichloroethyl-4-(p-tetradecyloxyphenyl)-2-methyl-buta-2,3-dienoate, which may be used as such in Step F, below.

Step F: 4-(p-tetradecyloxyphenyl)-2-methyl-buta-2,3-dienoic acid.

To a solution of 5.7 g. $\beta,\beta,\beta$-trichloroethyl-4-(p-tetradecyloxyphenyl)-2-methyl-2,3-butadienoate in 200 ml. absolute dimethylformamide (DMF) is added 24 g. of ether-wet-zinc-copper dust (prepared according to the procedure of E. LeGoff: J.O.C. 29, 2048 (1964), immediately after filtering; about 50% of the dust weight being residual ether. The reaction mixture is stirred at room temperature for 4 hours, filtered, diluted with 1 liter of ether and the organic phase washed extensively with 2N HCl, then with water, dried over anhydrous sodium sulfate, filtered, and the solvent removed i.v. From the residue is crystallized from pentane the title product, m.p. 85°–90° C.

Repeating the procedure of this Example but replacing the p-tetradecyloxyphenylacetic acid used in Step D, thereof, with an approximately equivalent amount of:

a) p-decyloxyphenylacetic acid;
b) p-octadecyloxyphenylacetic acid, or
c) p-hexadecyloxyphenylacetic acid;

there is accordingly obtained:

a) 4-(p-decyloxyphenyl)-2-methyl-buta-2,3-dienoic acid, m.p. 67°–75°, from pentane;
b) 4-(p-octadecyloxyphenyl)-2-methyl-buta-2,3-dienoic acid, m.p. 80°–85°, from pentane;
c) 4-(p-hexadecyloxyphenyl)-2-methyl-buta-2,3-dienoic acid, m.p. 80°–85°, from ether/pentane (10/1).

What is claimed is:

1. A compound of the formula

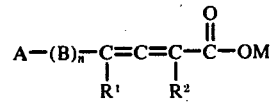

wherein n is 0 or 1;

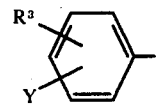

wherein Y is a hydrogen atom, alkyl having from 1 to 4 carbon atoms, alkoxy having from 1 to 24 carbon atoms, alkylthio having from 1 to 24 carbon atoms, halo having an atomic weight of from about 19 to 36, cyclohexyl, phenoxy or substituted or unsubstituted phenyl of the formula

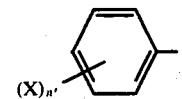

wherein X is a hydrogen atom, halo having an atomic weight of from about 19 to 36, alkoxy having from 1 to 4 carbon atoms or alkyl having from 1 to 4 carbon atoms;

n' is 1 or 2;

each of R1 and R2, independently, is a hydrogen atom or alkyl having from 1 to 4 carbon atoms;

R3 is a hydrogen atom, halo having an atomic weight of from about 19 to 36, or alkyl having from 1 to 4 carbon atoms; amd when n is 0, then A may also be

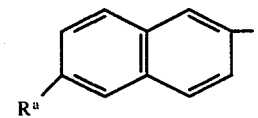

wherein R$^a$ is hydrogen, halo having an atomic weight of from about 19 to 36, alkyl having from 1 to 4 carbon atoms, alkoxy having from 1 to 4 carbon atoms, alkylthio having from 1 to 4 carbon atoms, or difluoromethoxy;

B is

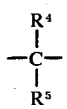

wherein each of R⁴ and R⁵ is, independently, alkyl having from 1 to 3 carbon atoms,
and M is a hydrogen atom, or a cation forming a non-toxic pharmaceutically acceptable salt,
provided that when n is 0, then Y and R³ are not both hydrogen atoms.

2. A compound of claim 1 in which n is 0.
3. A compound of claim 2 in which A is

4. A compound of claim 3 in which Y is at the para-position.
5. A compound of claim 4 in which R¹ is a hydrogen atom.
6. A compound of claim 5 in which R² is methyl.
7. A compound of claim 6 in which Y is alkoxy having from 1 to 24 carbon atoms or alkylthio having from 1 to 24 carbon atoms.
8. A compound of claim 7 wherein Y is alkoxy having from 1 to 4 carbon atoms or alkylthio having from 1 to 4 carbon atoms.
9. A compound of claim 8 wherein Y is alkoxy having from 1 to 4 carbon atoms.
10. The compound of claim 9 which is 4-(p-methoxyphenyl)-2-methylbuta-2,3-dienoic acid or a non-toxic pharmaceutically acceptable salt thereof.
11. A compound of claim 8 wherein Y is alkylthio having from 1 to 4 carbon atoms.
12. The compound of claim 11 which is 4-(p-thiomethylphenyl)-2-methyl-buta-2,3-dienoic acid or a non-toxic pharmaceutically acceptable salt thereof.
13. A compound of claim 6 wherein Y is alkoxy having from 5 to 24 carbon atoms.
14. A compound of claim 3 in which R1 is methyl.
15. A compound of claim 3 in which R1 is tert.-butyl.
16. A compound of claim 3 in which R1 is a hydrogen atom.
17. A compound of claim 1 in which n is 1.
18. A compound of claim 1 wherein A is

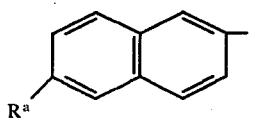

Ra being as defined.

19. A compound of claim 13 which is 4-(p-tetradecyloxyphenyl)-2-methyl-buta-2,3-dienoic acid.
20. A compound of claim 13 which is 4-(p-decyloxyphenyl)-2-methyl-buta-2,3-dienoic acid.
21. A compound of claim 13 which is 4-(p-octadecyloxyphenyl)-2-methyl-buta-2,3-dienoic acid.
22. A compound of claim 13 which is 4-(p-hexadecyloxyphenyl)-2-methyl-buta-2,3-dienoic acid.

23. A compound of claim 6 wherein Y is alkylthio having from 5 to 24 carbon atoms.
24. A compound of claim 1 in which A is

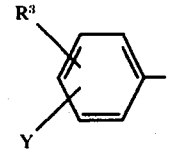

25. A compound of claim 6 wherein Y is alkoxy having from 5 to 16 carbon atoms.
26. A pharmaceutical composition useful as a hypolipidemic agent, in unit dosage form, comprising a non-toxic pharmaceutically acceptable solid carrier and as active ingredient from about 12.5 to 1000 milligrams of a compound of the formula

wherein n is 0 or 1;
wherein A is

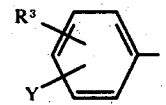

wherein Y is a hydrogen atom, alkyl having from 1 to 4 carbon atoms, alkoxy having from 1 to 24 carbon atoms, alkylthio having from 1 to 24 carbon atoms, halo having an atomic weight of from about 19 to 36, cyclohexyl, phenoxy or substituted or unsubstituted phenyl of the formula

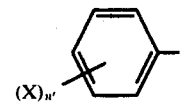

wherein X is a hydrogen atom, halo having an atomic weight of from about 19 to 36, alkoxy having from 1 to 4 carbon atoms or alkyl having from 1 to 4 carbon atoms;
n' is 1 or 2;
each of R¹ and R², independently, is a hydrogen atom or alkyl having from 1 to 4 carbon atoms;
R³ is a hydrogen atom, halo having an atomic weight of from about 19 to 36, or alkyl having from 1 to 4 carbon atoms, and
when n is 0 then A may also be

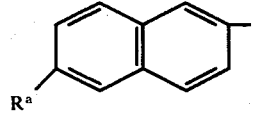

wherein Rª is hydrogen, halo having an atomic weight of from about 19 to 36, alkyl having from 1 to 4 carbon atoms, alkoxy having from 1 to 4 carbon atoms, alkylthio having from 1 to 4 carbon atoms, or difluoromethoxy;

B is

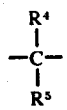

wherein each of $R^4$ and $R^5$ is, independently, alkyl having from 1 to 3 carbon atoms, and M is a hydrogen atom, or a cation forming a nontoxic pharmaceutically acceptable salt.

27. A composition of claim 26 which is in the form of a tablet.

28. A composition of claim 26 which is in the form of capsule.

29. A composition of claim 26 in which the active ingredient is 4-(p-tetradecyloxyphenyl)-2-methyl-buta-2,3-dienoic acid.

30. A method of lowering the level of lipids in the blood of a mammal comprising administrating to said mammal an amount effective in lowering the level of lipids in the blood of said mammal of a compound of the formula:

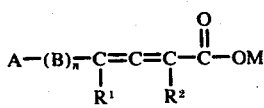

wherein $n$ is 0 or 1;
wherein A is

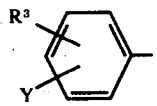

wherein Y is a hydrogen atom, alkyl having from 1 to 4 carbon atoms, alkoxy having from 1 to 24 carbon atoms, alkylthio having from 1 to 24 carbon atoms, halo having an atomic weight of from about 19 to 36, cyclohexyl, phenoxy or substituted or unsubstituted phenyl of the formula

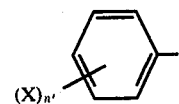

wherein X is a hydrogen atom, halo having an atomic weight of from about 19 to 36, alkoxy having from 1 to 4 carbon atoms or alkyl having from 1 to 4 carbon atoms;

$n'$ is 1 or 2;

each of $R^1$ and $R^2$, independently, is a hydrogen atom or alkyl having from 1 to 4 carbon atoms;

$R_3$ is a hydrogen atom, halo having an atomic weight of from about 19 to 36, or alkyl having from 1 to 4 carbon atoms, and when $n$ is 0 then A may also be

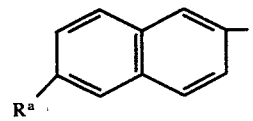

wherein $R^a$ is hydrogen, halo having an atomic weight of from about 19 to 36, alkyl having from 1 to 4 carbon atoms, alkoxy having from 1 to 4 carbon atoms, alkylthio having from 1 to 4 carbon atoms, or difluoromethoxy;

B is

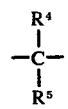

wherein each of $R^4$ and $R^5$ is, independently, alkyl having from 1 to 3 carbon atoms, and M is a hydrogen atom, or a cation forming a nontoxic pharmaceutically acceptable salt.

31. A method of claim 30 in which total daily dosage of the compound is from about 50 milligrams to about 2000 milligrams.

32. A method of claim 31 in which the compound is 4-(p-tetradecyloxyphenyl)-2-methyl-buta-2,3-dienoic acid.

* * * * *